United States Patent
Parameswaran et al.

(10) Patent No.: US 11,821,887 B2
(45) Date of Patent: Nov. 21, 2023

(54) SOIL HEALTH INDICATORS USING MICROBIAL COMPOSITION

(71) Applicant: TRACE GENOMICS, INC., Burlingame, CA (US)

(72) Inventors: Poornima Parameswaran, Menlo Park, CA (US); Sarah Placella, Oakland, CA (US); Di Wu, San Francisco, CA (US); Daniel S. Weaver, San Francisco, CA (US); Jenna Morgan Lang, Elk Grove, CA (US)

(73) Assignee: TRACE GENOMICS, INC., Ames, IA (US)

( * ) Notice: Subject to any disclaimer, the term of this patent is extended or adjusted under 35 U.S.C. 154(b) by 1270 days.

(21) Appl. No.: 16/258,415

(22) Filed: Jan. 25, 2019

(65) Prior Publication Data

US 2019/0227046 A1 Jul. 25, 2019

Related U.S. Application Data

(60) Provisional application No. 62/657,590, filed on Apr. 13, 2018, provisional application No. 62/622,071, (Continued)

(51) Int. Cl.
*G01N 33/24* (2006.01)
*C12Q 1/6888* (2018.01)
(Continued)

(52) U.S. Cl.
CPC ............. *G01N 33/24* (2013.01); *C12Q 1/689* (2013.01); *C12Q 1/6888* (2013.01);
(Continued)

(58) Field of Classification Search
CPC ............. G01N 33/24; G01N 2033/243; G01N 2033/245; C12Q 1/6888; C12Q 1/689;
(Continued)

(56) References Cited

U.S. PATENT DOCUMENTS 10,465,232 B1 *  11/2019  Wu ...................... C12Q 1/6806
10,762,982 B1 *   9/2020  Wu ...................... G06N 20/00
(Continued)

FOREIGN PATENT DOCUMENTS

WO   WO-2016025848 A1 *  2/2016  .......... A01B 79/005
WO   WO-2017096385 A1 *  6/2017  .......... C12Q 1/6888

OTHER PUBLICATIONS

European Patent Office, Extended European Search Report, European Patent Application No. 19743347.7, dated Oct. 12, 2021, 11 pages.
(Continued)

*Primary Examiner* — Ryan D Walsh
(74) *Attorney, Agent, or Firm* — Fenwick & West LLP

(57) ABSTRACT

An analytics system uses soil health indicators to determine metrics for soil samples. In an embodiment, the analytics system receives metadata describing a soil sample, where the metadata indicates one or more types of crops grown in a geographical location having the soil sample. The analytics system determines nucleic acid sequence reads of the soil sample. The analytics system determines taxonomic information of the nucleic acid sequence reads. The analytics system determines microbial composition of the soil sample using the taxonomic information. The analytics system determines reference metrics of soil samples from geographical locations in which the one or more types of crop were grown. The analytics system determines a metric of the soil sample using the microbial composition and the reference metrics. The analytics system transmits the metric to a client device.

20 Claims, 10 Drawing Sheets

Related U.S. Application Data filed on Jan. 25, 2018, provisional application No. 62/622,067, filed on Jan. 25, 2018, provisional application No. 62/622,063, filed on Jan. 25, 2018, provisional application No. 62/622,061, filed on Jan. 25, 2018, provisional application No. 62/622,062, filed on Jan. 25, 2018, provisional application No. 62/622,064, filed on Jan. 25, 2018, provisional application No. 62/622,070, filed on Jan. 25, 2018, provisional application No. 62/622,060, filed on Jan. 25, 2018, provisional application No. 62/622,059, filed on Jan. 25, 2018.

(51) Int. Cl.
    *G16B 20/00*     (2019.01)
    *G01S 19/42*     (2010.01)
    *C12Q 1/689*     (2018.01)
    *C12Q 1/6895*     (2018.01)
    *G16B 30/10*     (2019.01)

(52) U.S. Cl.
    CPC ........... *C12Q 1/6895* (2013.01); *G16B 20/00* (2019.02); *G01N 2033/243* (2013.01); *G01N 2033/245* (2013.01); *G01S 19/42* (2013.01); *G16B 30/10* (2019.02)

(58) Field of Classification Search
    CPC ...... C12Q 1/6895; G16B 20/00; G16B 30/10; G01S 19/42
    See application file for complete search history.

(56) References Cited

U.S. PATENT DOCUMENTS

| | | | |
|---|---|---|---|
| 2015/0284810 A1 | 10/2015 | Knight et al. | |
| 2016/0283651 A1* | 9/2016 | Knight | E21B 49/08 |
| 2019/0194742 A1* | 6/2019 | Wu | G16B 50/00 |
| 2020/0257997 A1* | 8/2020 | Mewes | A01G 22/00 |
| 2020/0271636 A1* | 8/2020 | Hartman | G16B 20/00 |
| 2020/0381081 A1* | 12/2020 | Zajdband | C12N 1/06 |
| 2021/0010993 A1* | 1/2021 | Shibata | A01B 79/005 |

OTHER PUBLICATIONS

Wolinska, A. et al. "Metagenomic Analysis of Some Potential Nitrogen-Fixing Bacteria in Arable Soils at Different Formation Processes." Microbial Ecology, vol. 73, No. 1, Jan. 2017, pp. 162-176.

Yuan, H. et al. "Abundance and Diversity of $CO_2$-Assimilating Bacteria and Algae Within Red Agricultural Soils are Modulated by Changing Management Practice." Microbial Ecology, vol. 70, May 10, 2015, pp. 971-980.

Zhao, J. et al. "Analysis of Unculturable Bacterial Communities in Tea Orchard Soils Based on Nested PCR-DGGE." World Journal of Microbiology and Biotechnology, vol. 28, Jan. 11, 2012, pp. 1967-1979.

Aranda, S. et al., "Microbial Communities Associated with the Root System of Wild Olives (*Olea europaea* L. subsp. *europaea* var. *sylvestris*) are Good Reservoirs of Bacteria with Antagonistic Potential Against Verticillium dahliae," Plant Soil, Feb. 20, 2011, vol. 343, pp. 329-345.

Calvo, J. et al., "Biological Control of Postharvest Spoilage Caused by Penicillium expansum and Botrytis cinereal in Apple by Using the Bacterium Rahnella aquatilis," International Journal of Food Microbiology, Feb. 15, 2007, vol. 113, No. 3., pp. 251-257.

Duniere, L. et al., "Bacterial and Fungal Core Microbiomes Associated with Small Grain Silages During Ensiling and Aerobic Spoilage," BMC Microbiology, Mar. 3, 2017, vol. 17, No. 1, pp. 1-16.

Nelson, M.B. et al., "Global Biogeography of Microbial Nitrogen-Cycling Traits in Soil," Proceedings of the National Academy of Sciences, Jul. 19, 2016, vol. 113, No. 29, pp. 8033-8040.

PCT International Search Report and Written Opinion, PCT Application No. PCT/US2019/015264, dated Apr. 15, 2019, 16 pages.

Reddy, B.V.B. et al., "eSNaPD: A Versatile, Web-Based Bioinformatics Platform for Surveying and Mining Natural Product Biosynthetic Diversity from Metagenomes," Chemistry & Biology, Aug. 14, 2014, vol. 21, pp. 1023-1033.

Fierer, N. et al., "Toward an Ecological Classification of Soil Bacteria," Ecology, 2007, vol. 88, No. 6, pp. 1354-1364.

MicroBIOMETER, "Welcome to the microBIOMETER," 8 pages, [Online] [Retrieved Apr. 9, 2019], Retrieved from the internet <URL: microbiometer.com>.

Solvita, "Solvita—providing indicators of soil biological processes," 2 pages, [Online] [Retrieved Apr. 9, 2019], Retrieved from the internet <URL: solvita.com/soil/>.

Ward Laboratories, Inc., "Haney/Soil Health Test Information Rev. 1.0," 4 pages, [Online] [Retrieved Apr. 9, 2019], Retrieved from the internet <URL: www.wardlab.com/haney-info.php>.

Ward Laboratories, Inc., "PLFA Information," 3 pages, [Online] [Retrieved Apr. 9, 2019], Retrieved from the internet <URL: www.wardlab.com/bio-testing-info.php>.

\* cited by examiner

SOIL HEALTH INDICATORS USING MICROBIAL COMPOSITION

CROSS REFERENCE TO RELATED APPLICATIONS

This application claims the benefit of priority to U.S. Provisional Application No. 62/622,059, filed on Jan. 25, 2018; U.S. Provisional Application No. 62/622,061, filed on Jan. 25, 2018; U.S. Provisional Application No. 62/622,067, filed on Jan. 25, 2018; U.S. Provisional Application No. 62/622,071, filed on Jan. 25, 2018; U.S. Provisional Application No. 62/622,060, filed on Jan. 25, 2018; U.S. Provisional Application No. 62/622,062, filed on Jan. 25, 2018; U.S. Provisional Application No. 62/622,063, filed on Jan. 25, 2018; U.S. Provisional Application No. 62/622,064, filed on Jan. 25, 2018; and U.S. Provisional Application No. 62/622,070, filed on Jan. 25, 2018, all of which are incorporated herein by reference in their entirety for all purposes. This application claims the benefit of priority to U.S. Provisional Application No. 62/657,590, filed on Apr. 13, 2018.

TECHNICAL FIELD

This disclosure generally relates to metrics of soil samples based on microbial composition of the soil samples.

BACKGROUND

The soil microbiome includes thousands of organisms, including bacteria, fungi, nematodes, and insects, among other microbes. Metagenomics (also referred to as environmental genomics or community genomics) may involve developing a profile of the microbiome detected in a biological sample such as soil. As one application, it is desirable to predict whether a farmer's field will produce a high or low crop yield, and whether the crops will develop disease. Further, it is challenging to determine the impact of microbe species (e.g., in soil) on crop yield and disease pressure.

BRIEF DESCRIPTION OF THE FIGURES

The disclosed embodiments have advantages and features which will be more readily apparent from the detailed description, the appended claims, and the accompanying figures (or drawings). A brief introduction of the figures is below.

SUMMARY

Figure 1:
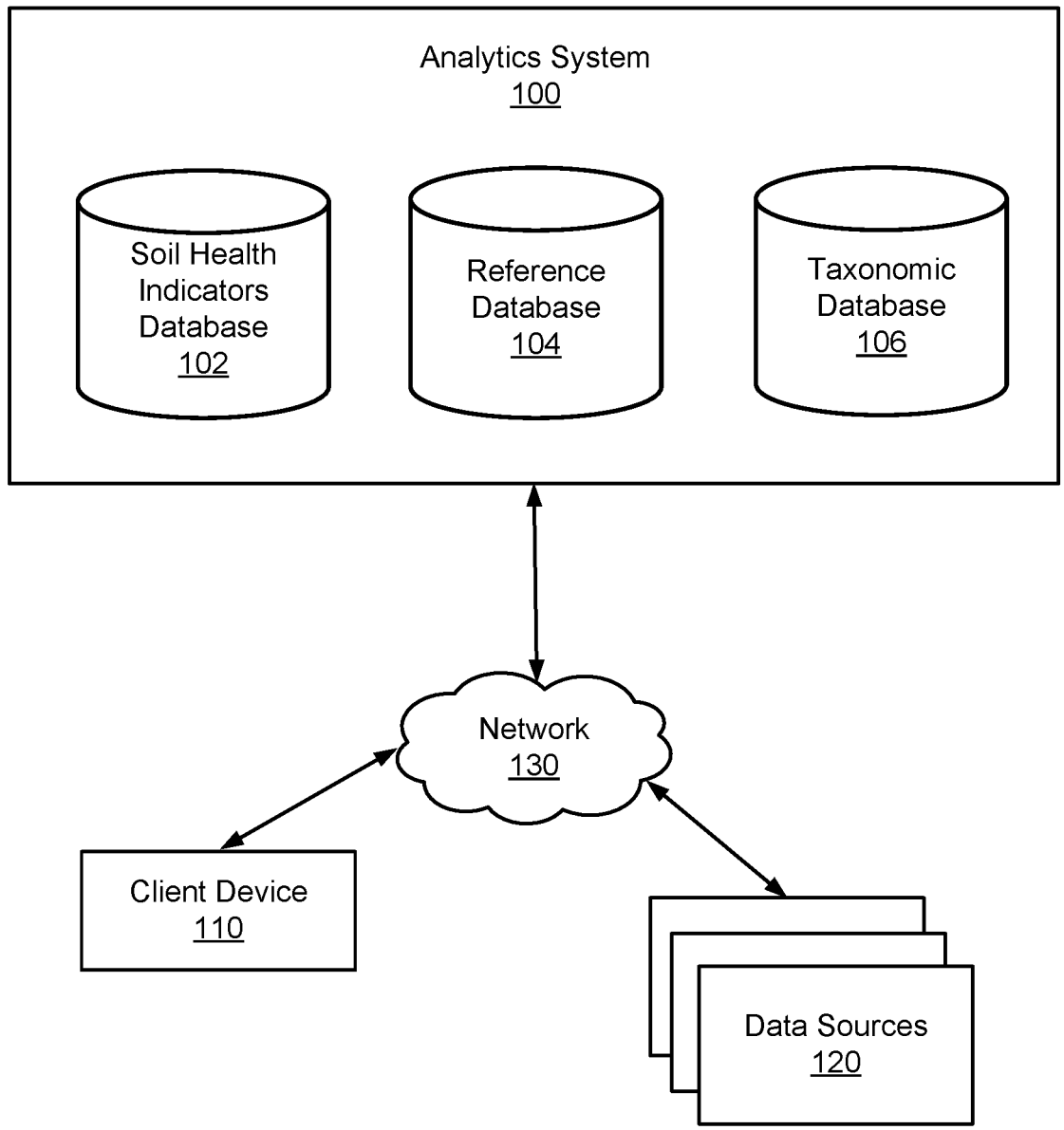
FIG. 1 illustrates an example system environment for an analytics system according to an embodiment.

An analytics system uses soil health indicators to determine metrics for soil samples, for example, indicating performance of crops grown in geographical locations having the soil samples. In various embodiments, a method includes receiving metadata describing a soil sample, where the metadata indicates one or more types of crops grown in a geographical location having the soil sample. The method further includes determining nucleic acid sequence reads of the soil sample. The method further includes determining, for each nucleic acid sequence read of at least a subset of the nucleic acid sequence reads, taxonomic information of the nucleic acid sequence read. The method further includes determining microbial composition of the soil sample using the taxonomic information. The method further includes determining reference metrics of soil samples from geographical locations in which the one or more types of crops were grown. The method further includes determining a metric of the soil sample using the microbial composition and the reference metrics. The method further includes transmitting the metric to a client device for display on a user interface.

In an embodiment, determining the metric of the soil sample comprises determining a value of a soil health indicator of the soil sample using the microbial composition. The method further includes determining a distribution of values of the soil health indicator for the soil samples using the reference metrics. The method further includes determining a percentile of the value with respect to the distribution of values.

In an embodiment, determining the metric of the soil sample further comprises determining one or more of oxygen status, nitrogen capacity, phosphorous capacity, potassium capacity, available carbon, or plant growth promoting bacteria of the soil sample. In another embodiment, determining the metric of the soil sample further comprises determining a level of root disease suppression of crops grown in the geographical location using the microbial composition. In another embodiment, determining the metric of the soil sample further comprises determining a level of post-harvest degradation of crops grown in the geographical location using the microbial composition.

In an embodiment, determining the microbial composition of the soil sample using the taxonomic information comprises determining a plurality of organisms in the soil sample. The method further includes determining, for each of the plurality of organisms, a count of the organisms in the soil sample. The method further includes normalizing the counts using a total count of organisms in the soil sample.

In an embodiment, determining the nucleic acid sequence reads of the soil sample comprises extracting microbial material from the soil sample. The method further includes generating nucleic acid sequence reads of the microbial material. The method further includes filtering the nucleic acid sequence reads.

In various embodiments, a method includes obtaining a soil sample from a geographical location. The method further includes receiving metadata indicating the geographical location. The method further includes determining a plurality of organisms in the soil sample. The method further includes determining, for each of the plurality of organisms, a measure of the organism in the soil sample. The method further includes determining microbial composition of the soil sample using the measures of the organisms. The method further includes determining reference metrics of soil samples from geographical locations within a threshold distance of the geographical location. The method further includes determining a metric of the soil sample using the microbial composition and the reference metrics. The method further includes transmitting the metric to a client device for display on a user interface.

In various embodiments, one or more processors may execute instructions stored by a non-transitory computer-readable storage medium to control a computer system to perform steps of any of the above methods. In various embodiments, a system includes a sampling tube for obtaining a soil sample from a geographical location. The system further includes one or more processors and a memory, the memory storing computer program instructions that when executed by the one or more processors cause the one or more processors to perform steps of any of the above methods.

DETAILED DESCRIPTION

I. Example System Overview

FIG. 1 illustrates an example system environment for an analytics system 100 according to an embodiment. The system environment shown in FIG. 1 includes the analytics system 100, a client device 110, and one or more data sources 120, which are connected to each other via a network 130 (e.g., the Internet). In other embodiments, different or additional entities can be included in the system environment. For instance, the system environment may include laboratory equipment to process samples and generate nucleic acid sequence reads (e.g., DNA or RNA fragments) of samples. Though only one client device 110 is shown in FIG. 1, the system environment may include additional client devices 110. The functions performed by the various entities of FIG. 1 may vary in different embodiments.

The analytics system 100 determines metrics of soil samples using soil health indicators. A soil health indicator is defined as a value of microbial driven function pertinent to agricultural production. A soil health indicator may reflect soil mineral and organic element availability, plant growth promoting factors, interaction with plant pathogens, crop performance, or other indicators of soil function or health. A soil health indicator may be derived by processing nucleic acids of a soil sample, for example, by sequencing deoxyribonucleic acid (DNA) or ribonucleic acid (RNA) to determine composition of microbes (also referred to herein as microorganisms or organisms) present in the soil sample, i.e., "microbial composition." Soil health indicators may be used to predict physical attributes of crops (e.g., stem size, plant height, or fruit size), crop yield, or resistance or crops or soil to certain diseases or pests.

The analytics system 100 may obtain soil samples from users (e.g., of the analytics system 100) such as farmers or other third parties (e.g., agriculture-related companies). In some embodiments, the analytics system 100 provides a sampling tube to a user, e.g., as part of a kit for collection of soil sample or related information. The user may collect a soil sample using the sampling tube and return the sampling tube (e.g., via mail or other delivery methods) to the analytics system 100 for processing. An interior of the sampling tube may be sterilized and may include a preservative solution, for example, to help maintain conditions of the soil sample or microbes present in the soil sample. The analytics system 100 may determine or indicate to a user a target volume, mass, or weight, of the soil sample to be collected using the sampling tube. The analytics system 100 may also provide sampling recommendations or protocols to users. For example, the sampling recommendations indicate a range of depth for soil collection (e.g., 0-6 inches below ground level), which may vary based on type of crop, geographical location, or other factors.

In some embodiments, the sampling tubes are associated with a label (e.g., barcode or QR code) for tracking or identification. The analytics system 100 may associate information describing users or soil samples with identification keys obtained soil samples. The information may include metadata, which is further described below with reference to FIG. 2A. The analytics system 100 may receive the information describing users or soil samples from client devices 110 of users, e.g., before, after, or along with receiving soil samples from users. The analytics system 100 may also receive the information from other forms of delivery such as a physically delivered document or device (e.g., mailed or provided in-person). By using the identification keys and associated information, the analytics system 100 may distinguish between multiple soil samples from the same user or different users. For instance, a user may provide soil samples from different geographical zones (e.g., geospatial units) of a field or farm, or from geographical zones in which different types of crops are grown. The analytics system 100 may homogenize multiple soil samples into a composite sample representative of a geographical zone. A field may be organized into geographical zones using grid cells or other configurations.

The analytics system 100 may determine a metric of a soil sample in view of a "crop community," that is, reference information associated with the soil sample. For example, the reference information includes data of other soil samples having similar conditions, in which same types of one or more crops were grown, treated with similar management or agricultural practices, or having other traits in common with the soil sample. The analytics system 100 stores metrics in the soil health indicators database 102.

The analytics system 100 stores reference information in the reference database 104. The analytics system 100 may receive reference information from one or more data sources 120 or client devices 110. For instance, users of the analytics system 100 provide soil samples and information (e.g., metadata) describing the soil samples that the analytics system 100 may use as reference information. The analytics system 100 may store information derived using the soil samples or metadata as reference information in the reference database 104. Moreover, the analytics system 100 may associate reference information with associated metadata. Accordingly, the analytics system 100 may perform lookup for reference information by querying the reference database 104 using metadata.

The analytics system 100 may provide metrics to users, e.g., for presentation on a client device 110 of a user. The analytics system 100 may also derive recommendations from metrics regarding agricultural techniques. Based on metrics or recommendations, farmers or other users may be informed as to a variety of actions that determine inputs or practices to use on fields, when to plant, where to plant, which crops to plant, or which varietals of those crops to plant, among other insights that may improve crop or soil health or performance.

A client device 110 comprises one or more computing devices capable of processing data as well as transmitting and receiving data over the network 130. For example, a client device 110 may be a desktop computer, a laptop computer, a mobile phone, a tablet computing device, an Internet of Things (IoT) device, or any other device having computing and data communication capabilities. The analytics system 100 may provide information to the client device 110 for presentation to a farmer or another user. The information may include metrics or recommendations determined by the analytics system 100 regarding soil samples or crops.

Though not shown in FIG. 1, the analytics system 100 may include one or more processors for manipulating and processing data, a network connection for communicating with other devices, and a non-transitory computer-readable storage medium for storing data, program code, or program instructions associated with various applications. It is noted that a storage medium may include volatile memory (e.g., random access memory) or non-volatile storage memory such as hard disks, flash memory, and external memory storage devices. The one or more processors may execute instructions to perform steps of one or more processes, e.g., the process described below with reference to FIG. 2A.

For purposes of explanation, this disclosure uses soil samples and the microbial composition of the soil samples generally as example use cases, though the embodiments described herein may be adapted for systems and methods using other types of biological samples or physical samples. For instance, the biological sample may be at least in part a liquid or aqueous sample used for growing plants in a hydroponics system. As a different example, the biological sample may be a sample of a gut microbiome of a subject (e.g., a human or another type of organism), and the analytics system 100 may determine metrics associated with physiology or other attributes of the subject.

II. Example Soil Health Indicators

The analytics system 100 may determine soil health indicators using information from one or more data sources 120. Example data sources 120 include publications, reference genome databases, microbe metadata databases, online microbial classification engines, metagenome sequencing projects and associated metadata, whole-genome sequencing projects, users of the analytics system 100, experiments or empirical data, or other public data repositories or tools. A data source 120 may be internal or external to the analytics system 100, e.g., associated with a third party. The analytics system 100 may integrate information (e.g., including unstructured data) from different types of data sources 120 to determine the soil health indicators. In some embodiments, the analytics system 100 may receive pre-determined soil health indicators or associated microbial functions from one or more data sources 120. In some use cases, the analytics system 100 may modify existing soil health indicators or derive new soil health indicators using one or more other soil health indicators.

The analytics system 100 stores soil health indicators in the soil health indicators database 102. In some embodiments, the analytics system 100 performs validation or benchmarking of soil health indicators using information from at least one data source 120. For example, the analytics system 100 performs statistical comparison of values of soil health indicators with expected values based on literature or empirical evidence from a reference data set.

In various embodiments, the analytics system 100 may determine measures of one or more particular types of microbes in a soil sample (e.g., microbial composition) to determine a soil health indicator. Furthermore, the analytics system 100 may determine an aggregate measure of the microbes. The aggregate measure may be based on relative abundance of one or more types of microbes. In an embodiment, the analytics system 100 divides an aggregate measure (e.g., count) of the one or more types of microbes in a soil sample by a total measure (e.g., count) of detected microbes in the soil sample. Moreover, the analytics system 100 may determine a ratio between the values of measures, scale values, or perform other transformation of values as part of calculations of a soil health indicator. Example types of microbes that may be considered in determination of soil health indicators are further described below.

II. A. Oxygen Status

In an embodiment, the analytics system 100 determines a soil health indicator using oxygen status, which may reflect level of aeration or saturation of a soil sample. Soil with low oxygen status may be prone to water logging and compaction. Responsive to determining that soil has low oxygen status, the oxygen status may be improved using one or more techniques, e.g., installing drainage tiles, not using heavy machinery to further compact the soil, and soil amendments such as gypsum. In an embodiment, the analytics system 100 determines a measure of microbes known to be obligate aerobes and another measure of microbes known to be obligate anaerobes. The analytics system 100 determines a ratio of the measures of obligate aerobes to obligate anaerobes. The analytics system 100 may determine a soil health indicator according to the ratio. Example microbes contributing to oxygen status are shown below in Table 1.

TABLE 1

Microbes contributing to oxygen status.

| Obligate aerobes | Obligate anaerobes |
|---|---|
| Spongiibacter | Methanolobus |
| Fluviicola | Anaeromusa |
| Citrobacter | Desulfurispora |
| Devriesea | Catonella |
| Flaviramulus | Heliobacterium |
| Sandarakinorhabdus | Methanobacterium |
| Neisseria | Peptoniphilus |
| Coraliomargarita | Spirochaeta |
| Microcystis | Thermovirga |
| Haloglycomyces | Oxalobacter |
| Gulbenkiania | Clostridiaceae |
| Mesonia | Natranaerobiales |
| Thiovulum | Collinsella |
| Peromyscus | Sulfuricurvum |
| Rheinheimera | Desulfobacterium |
| Chondromyces | Caloramator |
| Lampropedia | Ignavibacterium |
| Pinctada | Anaerobiospirillum |
| Nostoc | Methanolacinia |
| Dokdonia | Thermochromatium |
| Derxia | Propionispora |
| Gemmatimonas | Chloroflexus |
| Pirellula | Butyricimonas |
| Caldalkalibacillus | Senegalimassilia |
| Rhizobium | Coprothermobacter |

II. B. Nitrogen Capacity

In an embodiment, the analytics system 100 determines a soil health indicator using nitrogen capacity, which may represent a speed at which microbes in a soil sample cycle nitrogen. Responsive to determining that soil has low nitrogen capacity, microbes contributing to nitrogen levels may be added to the soil to help crops photosynthesize and grow. Ample nitrogen availability in soil may allow for reduced fertilizer nitrogen inputs, reducing costs and potential environmental problems from nitrogen waste. The analytics system 100 determines a measure of microbes in a soil sample known to be nitrifiers, for example, based on information from a data source 120 or the reference database 104. For instance, the analytics system 100 classifies that microbes having a genus beginning with "nitro" as known nitrifiers. In another example, the analytics system 100 aggregates measures of ammonia oxidizers and nitrate oxidizers. The analytics system 100 may determine a soil health indicator according to the measure of nitrifiers or microbes contributing to nitrification.

II. C. Phosphorous Capacity

In an embodiment, the analytics system 100 determines a soil health indicator using phosphorus capacity, which may represent a speed at which microbes in a soil sample cycle phosphorous. Responsive to determining that soil has low phosphorus capacity, soluble phosphorus or microbes contributing to phosphorous levels may be added to the soil to help crops grow. In addition, excess phosphorous may runoff and cause eutrophication or other unwanted environmental consequences. In an embodiment, the analytics system 100 determines a measure of microbes in a soil sample empirically known to increase phosphorous availability, or known to solubilize phosphorous, e.g., phytases, alkaline phosphatase, or acid phosphatases. The analytics system 100 may also determine a measure of mineral phosphorous solubilization to determine phosphorous availability. Example microbes contributing to phosphorus capacity are shown below in Table 2.

TABLE 2

Microbes contributing to phosphorus capacity.

| | Genus | *Pseudomonas* |
|---|---|---|
| | | *Bacillus* |
| | | *Micrococcus* |
| | | *Flavobacterium* |
| | | *Fusarium* |
| | | Sclerotium |
| | | *Aspergillus* |
| | | *Penicillium* |
| | | Discosia |
| | | Rhizobium |
| | | Gordonia |
| | | *Enterobacter* |
| | | Rahella |
| | | Pantoea |
| | | Pseudomonas |
| | | *Aspergillus* |
| | | *Penicillium* |
| | | *Trichoderma* |
| | | *Emmericella* |
| | | Telephora |
| | | Suillus |
| | | Klebsiella |
| | | Prevotella |
| | | Treponema |
| Species | | *Citrobacter braakii* |
| | | *Escherichia coli* |
| | | *Lactobacillus amylovorus* |
| | | *Megasphaera elsdenii* |
| | | *Mitsuokella multiacidus* |
| | | *Mitsuokella jalaludinii* |
| | | *Obesumbacterium proteus* |
| | | *Pantoea agglomerans* |
| | | *Selenomonas ruminantium* |

TABLE 2-continued

Microbes contributing to phosphorus capacity.

| Genus | *Pseudomonas* |
|---|---|
| | *Yersinia intermedia* |
| | *Burkholderia vietnamiensis* |
| | *Citrobacter freundi* |
| | *Proteus mirabali* |
| | *Serratia marcenscens* |
| | *Emericella rugulosa* |
| | *Chaetomium globosum* |
| | *Burkholderia cepacia* |
| | *Enterobacter aerogenes* |
| | *Enterobacter cloacae* |
| | *Sporotrichum thermophile* |

II. D. Potassium Capacity

In an embodiment, the analytics system 100 determines a soil health indicator using potassium capacity, which may represent a speed at which microbes in a soil sample cycle potassium. Responsive to determining that soil has low potassium capacity, microbes contributing to potassium levels may be added to the soil to help crops grow. In an embodiment, the analytics system 100 determines a measure of microbes in a soil sample empirically known to solubilize potassium or known to produce organize acids, e.g., microbes having phylum Actinobacteria, or genus *Aspergillus, Bacillus*, or *Clostridium*.

II. E. Available Carbon

In an embodiment, the analytics system 100 determines a soil health indicator using available carbon, which may serve as a food source for microbes or as a source of nutrients for crops. Responsive to determining that soil has low available carbon (e.g., labile organic material), carbon supplements or activated carbon biofertilizers may be added to the soil to help crops grow. In an embodiment, the analytics system 100 determines measures of one or more of Betaproteobacteria and Bacteroidetes in a soil sample to determine a level of available carbon in the soil sample.

II. F. Plant Growth Promoting Bacteria

In an embodiment, the analytics system 100 determines a soil health indicator using plant growth promoting bacteria. Using the information from the reference database 104, the analytics system 100 may determine microbes that are bacteria known to increase plant growth or otherwise improving crop yield. Example plant growth promoting bacteria include acdS 1-aminocyclopropane-1-carboxylate deaminase containing taxa, *rhizobia*, free-living nitrogen fixers, nitrogen-fixing symbiotic Actinobacteria (e.g., having genus *Frankia*), rhizobacteria, and microbes having particular species or genus as shown below in Table 3.

TABLE 3

Microbes promoting plant growth.

| Species | *Serratia marcescens* |
|---|---|
| | *Bacillus subtilis* |
| | *Bacillus amyloliquefaciens* |
| | *Bacillus pumilus* |
| | *Bacillus pasteurii* |
| | *Paenibacillus polymyxa* |
| | *Pseudomonas fluorescens* |
| | *Pseudomonas aeruginosa* |
| | *Serratia liquefaciens* |
| | *Alcaligenes faecalis* |
| | *Bacillus cereus* |
| | *Enterobacter hormaechei* |
| | *Pseudomonas brassicacearum* |
| | *Pseudomonas marginalis* |

TABLE 3-continued

Microbes promoting plant growth.

| | |
|---|---|
| | *Pseudomonas oryzihabitans* |
| | *Pseudomonas putida* |
| | *Alcaligenes xylosoxidans* |
| | *Bacillus cepacia* |
| | *Agrobacterium rubi* |
| | *Burkholderia gladii* |
| | *Bacillus megaterium* |
| | *Azospirillum amazonense* |
| | *Azospirillum lipoferum* |
| | *Azospirillum brasilense* |
| | *Azospirillum halopraeferens* |
| | *Azospirillum irakense* |
| Genus | *Acinetobacter* |
| | *Pantoea* |
| | *Rhodococcus* |
| | *Azospirillum* |

II. G. Root Disease Resistance

In an embodiment, the analytics system 100 determines a soil health indicator using a level of root disease resistance. Soil with greater root disease resistance is more likely to naturally suppress or combat pathogens known to attack roots of plants. Example microbes known to contribute to root disease resistance are shown below in Table 4.

TABLE 4

Microbes contributing to root disease resistance.

| | |
|---|---|
| Genus | *Myxococcus* |
| | *Trichoderma* |
| | *Gliocladium* |
| | *Penicillium* |
| | *Pseudomonas* |
| | *Acremonium* |
| | *Bacillus* |
| | *Burkholderia* |
| | *Sphingomonas* |
| | *Gemmatimonas* |
| Family | Xylariaceae |
| | Hypocreaceae |
| | Bionectriaceae |

II. H. Post-Harvest Disease Susceptibility

In an embodiment, the analytics system 100 determines a soil health indicator using a level of post-harvest disease susceptibility. For example, fruit vegetables harvested from soils with high post-harvest disease susceptibility may be more likely to degrade in quality during shipping or storage. The analytics system 100 may determine a measure of microbes in a soil sample known to cause or be associated with diseases or conditions affected crop quality post-harvest. In an embodiment, the analytics system 100 determines that microbes having genus of *Botrytis*, *Botryotinia*, *Alternaria*, *Mucor*, *Rhizomucor*, or *Rhizopus*, contribute to increased post-harvest disease susceptibility.

III. Example Process Flows

Figure 2A:
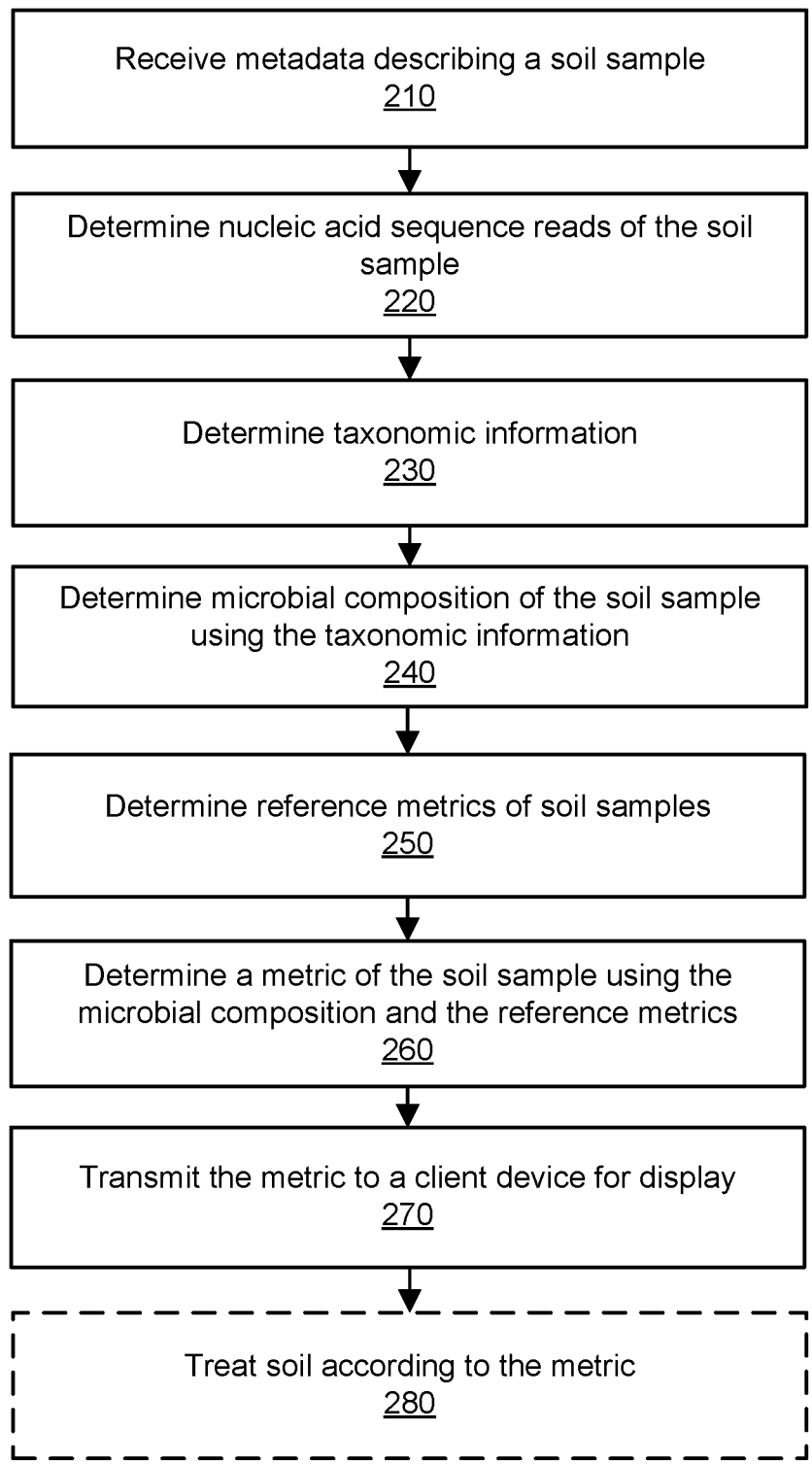
FIG. 2A illustrates an example process for providing a metric of a soil sample according to an embodiment.
Figure 2B:
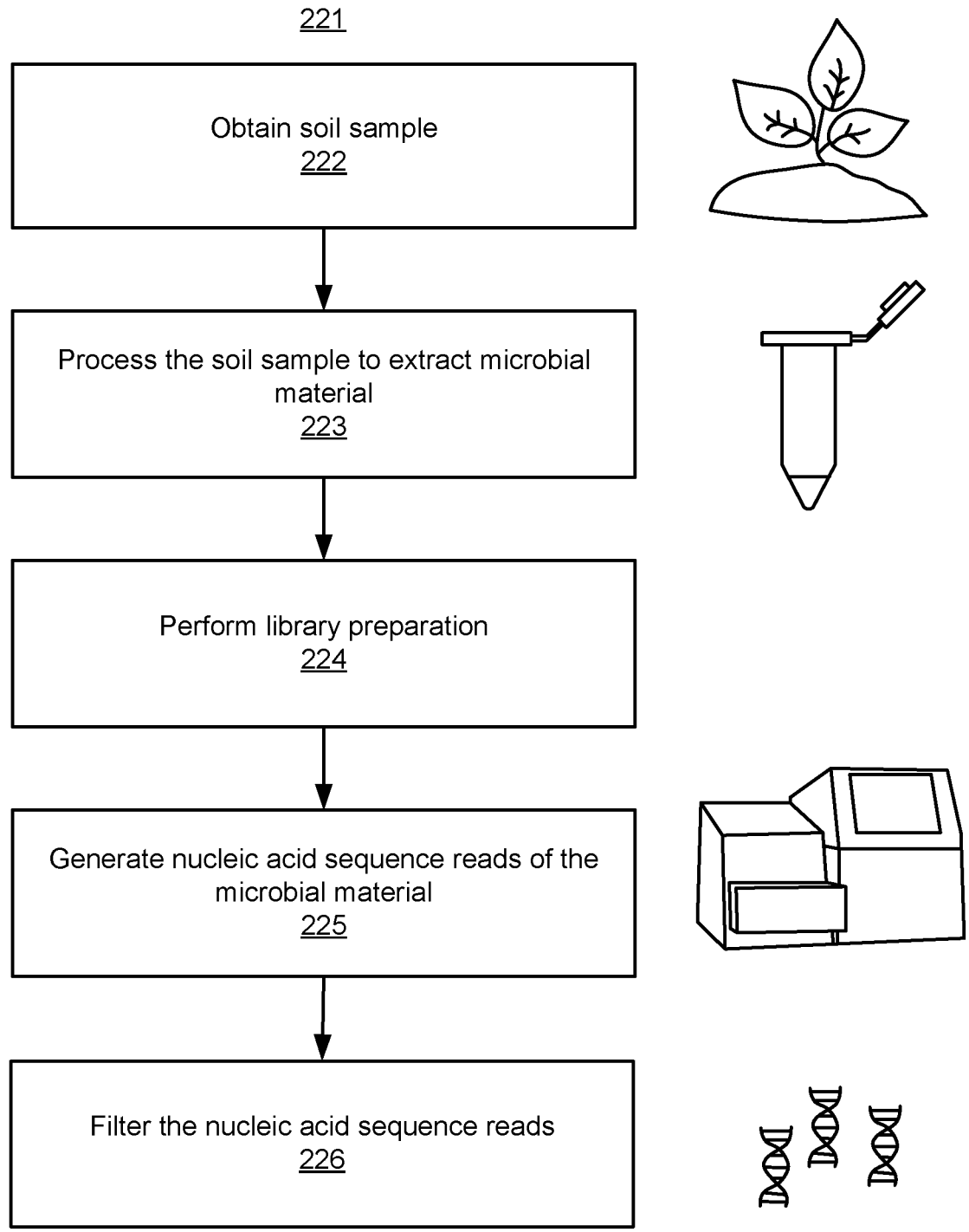
FIG. 2B illustrates an example process for determining nucleic acid sequence reads of a soil sample according to an embodiment.

FIG. 2A illustrates an example process 200 for providing a metric of a soil sample according to an embodiment. FIG. 2B illustrates an example process 221 for determining nucleic acid sequence reads of a soil sample according to an embodiment. In various embodiments, the processes 200 or 221 are used by the analytics system 100 within the system environment in FIG. 1. The processes may include different or additional steps than those described in conjunction with FIG. 2A-B in some embodiments or perform steps in different orders than the order described in conjunction with FIG. 2A-B.

The analytics system 100 receives 210 metadata describing a soil sample. In some embodiments, the metadata may indicate one or more crops grown in a geographical location having the soil sample. Example types of crop include corn, lettuce, soybean, strawberry, potato, among other types of fruits, vegetables, or plants. The cropping history of a geographical location may include a rotation of multiple types of crops, e.g., based on seasonality or the geographical location. In other embodiments, the metadata may indicate other information such as the geographical location, a current crop grown in the geographical location, or attributes describing treatment of the soil sample. The geographical location may be defined by global positioning system (GPS) coordinates or other suitable information, e.g., a neighborhood, city, state, country, or identification number. Example attributes describing treatment of the soil sample include agricultural techniques such as no-till farming, use of a cover crop to manage soil qualities (e.g., erosion, fertility, disease, or biodiversity), carbon farming, strip-till, and conservation agriculture. Attributes may also describe water or fertilizer usage, whether a crop is organic, temperature, precipitation, or climate, among other types of crop or soil related information. Metadata may also indicate a soil type of the soil sample. The analytics system 100 may process soil samples of different soil types, for example, sandy, silt, clay, loamy, and peat, among others.

The analytics system 100 determines 220 nucleic acid sequence reads of the soil sample. Referring now to FIG. 2B, the process 221 may be performed to determine the nucleic acid sequence reads as part of the process 200 of FIG. 2A.

A soil sample is obtained 222 using any of the methods previously described with reference to FIG. 1, e.g., the analytics system 100 receives the soil sample from a farmer using a sampling tube. The soil sample is processed 223 to extract microbial material (also referred to as microbial genetic material). In some embodiments, the soil sample may be stored at −80 degrees Celsius prior to extraction of the microbial material. In an embodiment, the soil samples are added to extraction vessels by mass, volume, suspension volume, or another measurement. Cell lysis is performed on the soil samples to release the microbial material including intracellular nucleic acids. Cell lysis may include chemical (buffers or salts), mechanical (bead beating or sonication), or thermal (e.g., freezing, free-thaw cycling, or microwaving) processes. Soil and the released microbial material are separated. Cellular debris may be removed using chemical precipitation or centrifugation. Additionally, contaminants may be removed using precipitation and elution of the microbial material. The microbial material may be prepared using fluorescent dyes or gels for downstream assay or spectroscopy.

In some embodiments, the nucleic acids of the microbial material may be processed prior to library preparation. For example, target genes or genome regions may be enriched for polymerase chain reaction (PCR) amplification or amplicon sequencing. Targeted DNA primers may be used to flank a region of interest. Alternatively, in shotgun sequencing, the microbial material may be prepared for sequencing of the entire content, e.g., microbes in a crop community of the processed soil sample. In some use cases, DNA fragment size may be controlled chemically using size selection gel beads, physically using ultrasonic shearing, or enzymatically using transposase fragmentation.

Sequencing library preparation is performed 224 on the extracted microbial material. Library preparation may include attaching sequencing adapters or tags to nucleic acids to facilitate reading of the nucleic acids. Sequencing tags may be unique to each sample (e.g., serving as a barcode) and enable identification of sequenced data associated with each sample in a multiplexed run with multiple samples. Libraries may also be prepared using other suitable methods such as ligation or transposase. In some use cases, library preparation includes protocols from sequencer original equipment manufacturers (OEMs), third party kit providers, or other resources. The analytics system 100 may store data from library preparation for future processing or analyses of other soil samples.

Once the sequencing library is prepared, the library or a portion of the library can be sequenced such that nucleic acid sequence reads of the microbial material are generated 225 using one or more techniques. In some embodiments, a sequencer performs sequencing (e.g., of DNA or RNA) and outputs sequence reads of the microbial material. The sequencer may provide the output sequence reads to the analytics system 100. The sequencer can be communicatively coupled to the analytics system 100 through a wireless, wired, or a combination of wireless and wired communication technologies. In some embodiments, the nucleic acid sequence reads are generated using next generation sequencing (NGS) techniques including synthesis technology (ILLUMINA®), pyrosequencing (454 LIFE SCIENCES), ion semiconductor technology (Ion Torrent sequencing), single-molecule real-time sequencing (PACIFIC BIOSCIENCES®), or nanopore sequencing (OXFORD NANOPORE TECHNOLOGIES). DNA sequencing can also be performed as described in Sanger et al. (PNAS 74:5463, (1977)) and the Amersham International plc sequencing handbook, which methods are incorporated by reference herein. The analytics system 100 filters 226 the nucleic acid sequence reads, e.g., for quality control. In particular, the analytics system 100 may remove sequence reads having artificial multiplexing barcode or adapter sequences. In addition, the analytics system 100 may determine that a sequence read is low quality responsive to determining that a length of the sequence read is less than a threshold value, the sequence read includes at least a threshold number of ambiguous bases, or a read quality score (e.g., determined using a third-party tool) is less than a threshold score. The analytics system 100 may discard low quality sequence reads. The analytics system may also partition sequence reads using identification barcodes for demultiplexing batches of sequence reads generated from multiple samples.

Returning to FIG. 2A, the analytics system 100 may use the sequence reads to identify presence of one or more types of microbes in the soil sample. For example, the analytics system 100 can align the sequence read to one or more reference genomes that are stored in the reference database 104 (e.g., reference genomes of microbes commonly found in soil or otherwise known). The reference genome provides the context as to the position in a genome from which the nucleic acid fragment originates. The analytics system 100 can align the sequence reads to known sites in the sequences of different organisms, which may be typically found in soil samples. Based on this, the analytics system 100 can identify which microbes are present in the soil sample, and can also gain information about microbes that are not present.

The analytics system 100 then determines 230 taxonomic information of the microbes associated with the nucleic acid sequence reads. The analytics system 100 may store the taxonomic information in the taxonomic database 106, e.g., in a table or another suitable type of data structure. In one embodiment, for each nucleic acid sequence read of at least a subset of the nucleic acid sequence reads, the analytics system 100 determines taxonomic information of the microbe (organism) associated with the nucleic acid sequence read. The taxonomic information may indicate a name, metadata, traits, or a functional group of the microbe. The name may correspond to a taxonomic rank, e.g., domain, kingdom, phylum, class, order, family, genus, or species.

In other embodiments, the analytics system 100 determines organism metadata in addition or alternatively to determining the taxonomic information. The analytics system 100 classifies reads of nucleic acid sequences into functional groups based on the organism metadata. Organism metadata indicate presence of a trait of an organism to which a read is taxonomically assigned. The analytics system 100 may determine organism metadata for classification using one or more data sources 120 or the reference database 104.

Figure 8:
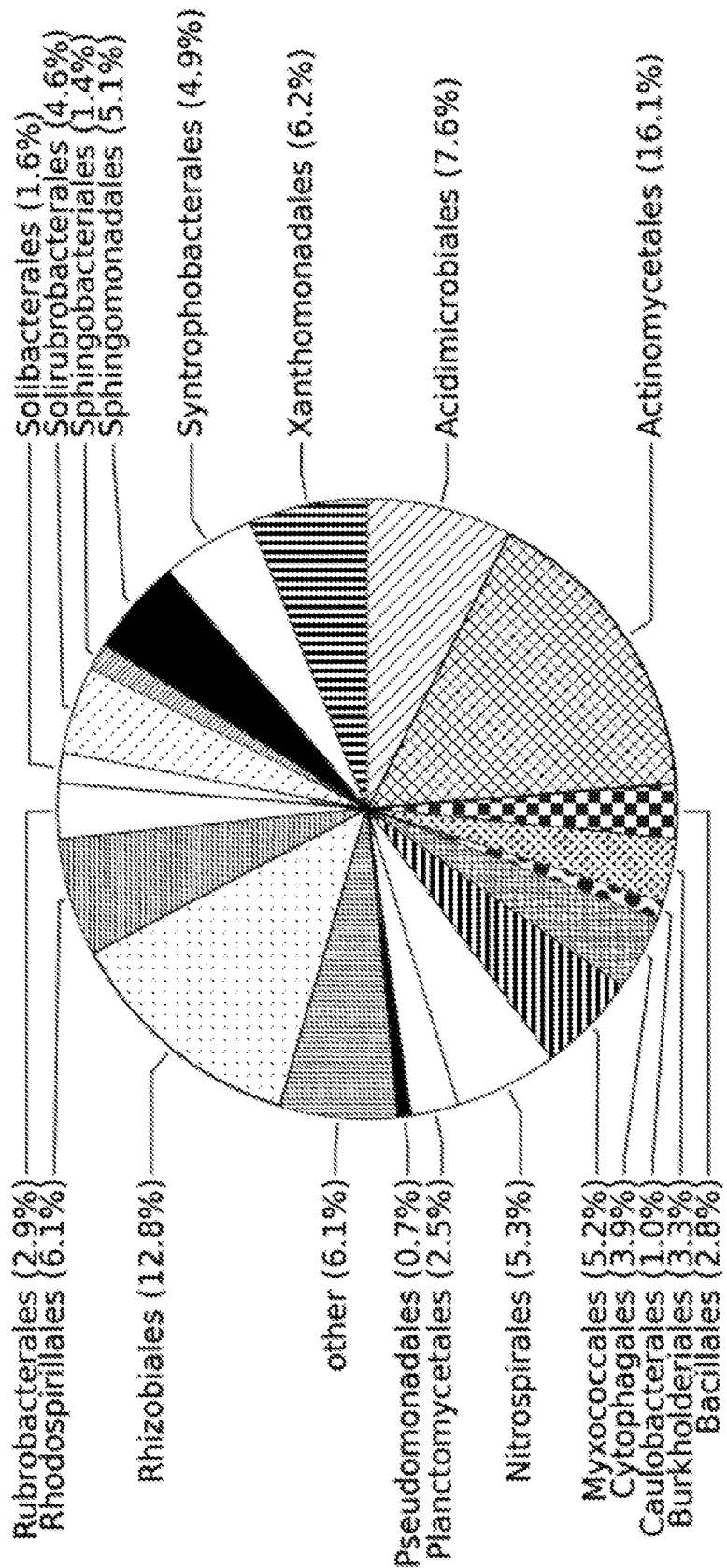
FIG. 8 is a diagram of an example microbial composition of healthy soil according to an embodiment.
Figure 9:
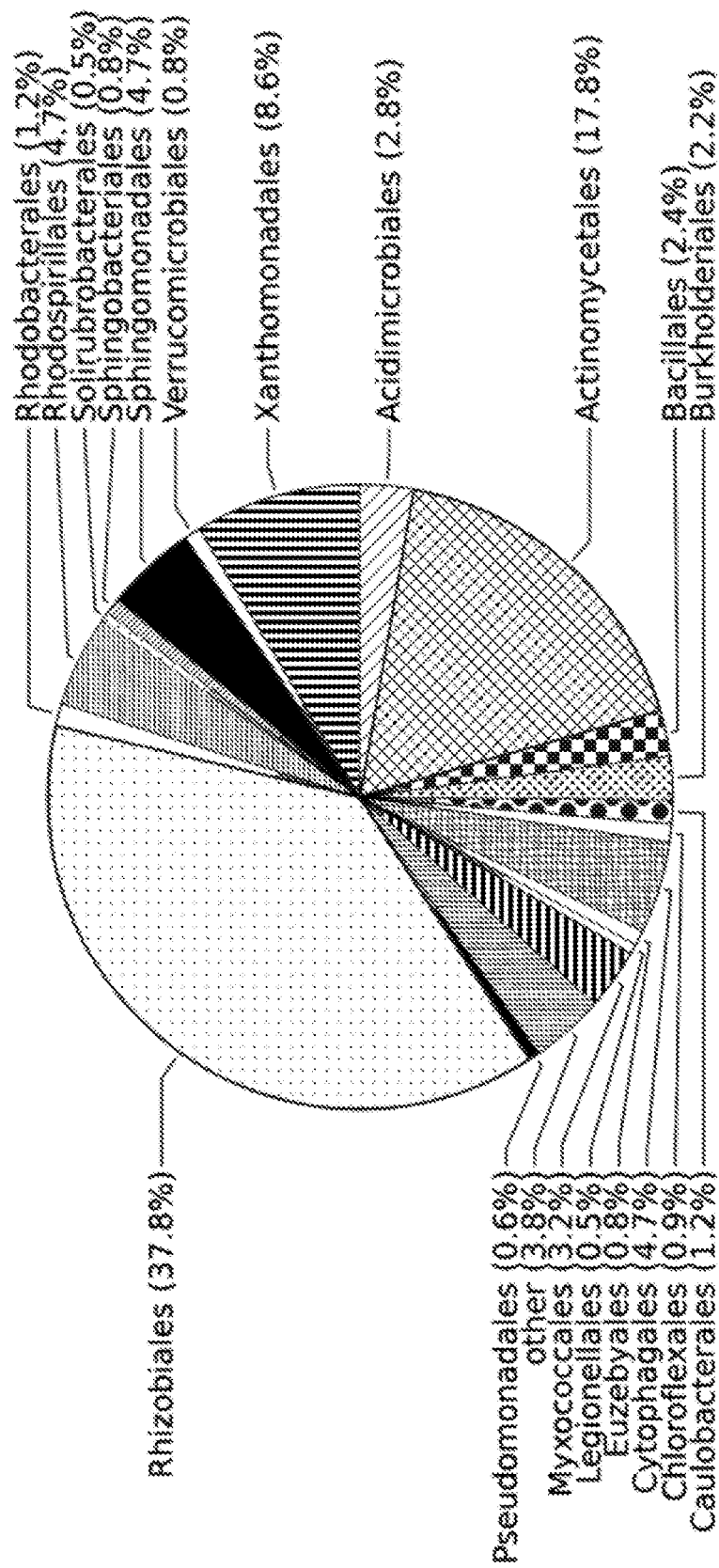
FIG. 9 is a diagram of an example microbial composition of compost according to an embodiment.

The analytics system 100 determines 240 microbial composition of the soil sample using the taxonomic information. As described above, the analytics system 100 may determine the taxonomic information using the nucleic acid sequence reads along with one or more reference genomes. Example microbial compositions determined by the analytics system 100 are shown in FIGS. 8-9. In an embodiment, the analytics system 100 uses the taxonomic information to determine organisms present in the soil sample. For each of the present organisms, the analytics system 100 determines a measure (e.g., count) of the organism in the soil sample. The analytics system 100 may normalize the measure using a total measure of organisms in the soil sample, e.g., by dividing individual counts over a total count. In other embodiments, the analytics system 100 may normalize based on total sequence reads per sample, total annotations, total genome copies measured, total genus count, or total count of organisms classified based on another taxonomic rank (e.g., phylum, family, etc.). Normalization of the counts may account for sources of systematic variation or error in the counts, e.g., as stored in a table or another type of data structure. The analytics system 100 aggregates the normalized measures to construct the microbial composition. The analytics system 100 may store the microbial composition (e.g., as a table of normalized counts) in the taxonomic database 106. In other embodiments, instead of using nucleic acid sequencing, the analytics system 100 determines counts of organisms using quantitative PCR (qPCR) or Droplet Digital PCR (ddPCR).

The analytics system 100 determines 250 reference metrics of soil samples, e.g., from geographical locations or communities in which the one or more types of crop were grown. The reference metrics may include a distribution of values of soil health indicators retrieved from the soil health indicators database 102. Generally, the analytics system 100 may retrieve the reference metrics (or "crop community values") from soil health indicators determined for soil samples of other users of the analytics system 100 or from other sources of reference information. For example, the analytics system 100 determines reference metrics from other soil samples within a threshold distance (e.g., 10, 50, 100, or 200 miles) from the soil sample. In a different example where the metadata indicates cropping history, the analytics system 100 determines reference metrics from other soil samples in which at least one common crop is currently or was previously grown. Furthermore, the analytics system 100 may determines reference metrics from other soil samples treated with similar or same agricultural techniques as those treated to the soil sample.

The analytics system 100 determines 260 a metric of the soil sample using the microbial composition and the reference metrics. In an embodiment, the analytics system 100 determines a value of a soil health indicator using the microbial composition. As previously described, the soil health indicator may be a function of measures of one or more types of microbes, e.g., associated with oxygen status, nitrogen capacity, phosphorous capacity, potassium capacity, available carbon, plant growth promoting bacteria, root disease resistance, or post-harvest disease susceptibility. The analytics system 100 may determine the metric by performing one or more statistical transformations of the value of the soil health indicator. For example, the analytics system 100 determines a percentile of the value of the soil health indicator with respect to a distribution of soil health indicator values, as provided by the reference metrics. The percentiles may be scaled from 0 to 100%. In other embodiments, the analytics system 100 scales the value of soil health indicator to a different range such as 0.0 to 1.0 or 0 to 10, which may not necessarily be a percentile range.

In some embodiments, the analytics system 100 determines ranges of the reference metrics. The analytics system 100 may organize values of a soil health indicator for a set of fields (e.g., based on reference information of a community), within a threshold geographical location (or having another common characteristic or metadata), into buckets of a range of percentiles. For example, one bucket includes the top 10% of values of a soil health indicator associated with capacity of a given nutrient. Another bucket includes the next 10% of values of the soil health indicator, and so forth until a bucket including the bottom 10% of values of the soil health indicator. In other embodiments, the buckets may be associated with different intervals such as 20%, 25%, or 50%. When determining the metric for the soil sample, the analytics system 100 may identify a bucket to which the value of the soil health indicator of the soil sample belongs. For instance, the analytics system 100 determines that the value, of the soil health indicator of the soil sample collected from a geographical location, falls within the top 10% of values for nitrogen capacity of farms in the geographical location. Accordingly, the analytics system 100 may determine "0-10%" or "10%" as the metric.

In a different embodiment, the analytics system 100 may determine the metric according to standard deviations of the value of the soil health indicator away from an average value of the soil health indicator based on reference metrics. In some embodiments, the analytics system 100 may normalize the reference metrics to a logarithmic scale.

Figure 7:
FIG. 7 illustrates an example user interface with metrics of soil samples according to an embodiment.

The analytics system 100 transmits 270 the metric to a client device 110 for display on a user interface, e.g., as shown in FIG. 7. In some embodiments, the analytics system 100 provides the metric for display in context of reference metrics. For example, a bar graph indicates an average value of a soil health indicator for farms in a geographical location from which the soil sample was collected. The user interface shows whether the metric is above, at, or below the average value. In other embodiments, the user interface may show other thresholds in varying levels of granularity, e.g., top 10% of values or top quartile or values of the soil health indicator based on reference metrics. In some embodiments, the analytics system 100 may provide a notification to a user responsive to determining that the metric is below a threshold value such as the average value. The notification may inform the user that treatment should be applied to a field, e.g., to supplement a nutrient at low availability. By providing soil health indicators with community context, users of the analytics system 100 may determine health or performance of their fields relative to other comparable fields in terms of geographical location, cropping history, soil treatments, among other traits encoded in metadata stored by the analytics system 100. Additionally, the analytics system 100 may store determined metrics or soil health indicators in the soil health indicator database 102. The analytics system 100 may use these metrics or soil health indicators as reference metrics for subsequent determination of new metrics for other soil samples.

In an optional step in some embodiments, soil at the geographical location (from which the soil sample is obtained) is treated 280 according to the metric. For example, the metric may indicate that a crop is less resistant to root disease in comparison to an average metric of root disease for crops of the same or similar type, or crops grown in similar conditions or geographical locations. In response, a farmer may provide additional fertilizer, fumigation, water, cover crop, or other types of substances to the crop or soil to mitigate possible negative effects of disease, or to modify levels of oxygen, nitrogen, phosphorous, potassium, or carbon of the soil. In some embodiments, the analytics system 100 may receive new soil samples from a field after a treatment is applied to the field, e.g., according to metrics or recommendations provided by the analytics system 100. The analytics system 100 determines updated metrics (or recommendations) by processing the new soil samples and transmits the updated metrics to the client device 110 for presentation. Thus, the farmer may evaluate effect of the treatment by comparing the metrics before and after applying the treatment. The analytics system 100 may also receive additional soil samples from a field continuously over a period of time (e.g., weekly, monthly, or at arbitrary sample collection times) and track performance or health of the field by identifying trends in the determined metrics. The analytics system 100 may determine trends in context of crop community data.

In one embodiment, the analytics system 100 may provide a command to a client device 110 or another type of device to automatically treat the soil with a treatment loaded onto the device. For instance, the device is a manned or autonomous tractor for applying fertilizer, water, or other substance to soil or crops.

IV. Example Metrics

FIGS. 3-6 are diagrams including example metrics of soil samples determined by the analytics system 100 using any of the processes described herein. The soil samples were obtained from fields or farms having similar geographical locations and cropping conditions, aside from any stated differences between control and test samples. The example metrics are provided as values of soil health indicators on a scale from 0 to 100, though some diagrams may have truncated y-axis values for the soil health indicators.

Figure 3:
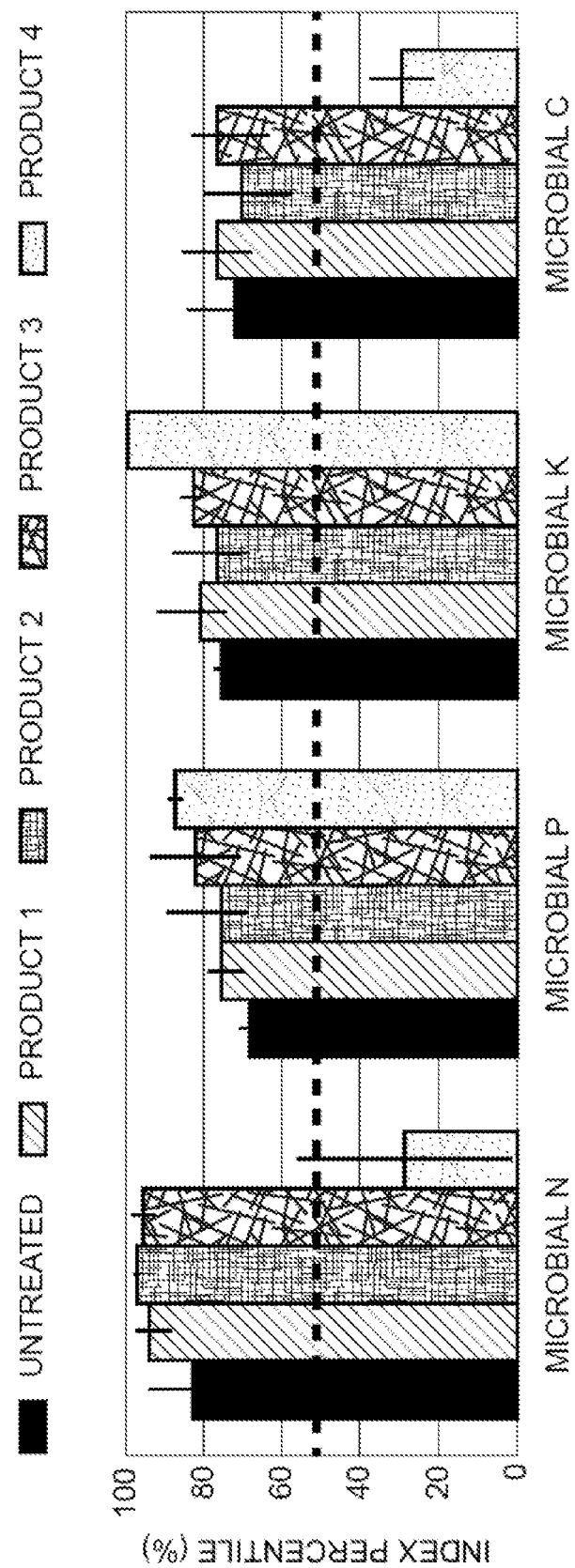
FIG. 3 is a diagram including example metrics of soil samples treated with a fumigant according to an embodiment.

FIG. 3 is a diagram including example metrics of soil samples treated with a fumigant according to an embodiment. The soil samples were collected from a strawberry field in the Central Coast of California. The example metrics show effects of various products applied to soil. In particular, soil samples treated with "product 4," a fumigant, have decreased nitrogen capacity and carbon availability, relative to an untreated control sample and soil samples treated with other types of products. Samples treated with the fumigant also have increased cycling capacity of phosphorous and potassium, relative to the other samples. Different compositions of the products may stimulate growth of different microbial communities, e.g., based on availability of certain resources from applied products or treatments.

Figure 4:
FIG. 4 is a diagram including example metrics of soil samples of lettuce crop infected with a pathogen according to an embodiment.

FIG. 4 is a diagram including example metrics of soil samples of lettuce crop infected with a pathogen according to an embodiment. The soil samples were collected from ten fields in Yuma, Arizona, which included romaine lettuce and iceberg lettuce crops. In comparison to the "healthy" soil samples, the "not healthy" soil samples with a pathogen infection have lower nitrogen capacity and potassium capacity. The lower availability of nutrients may contribute to an increased vulnerability of crops grown in the soil sample to pathogen infections. In other words, nutrient related metrics may at least partially explain differences between healthy and not healthy (e.g., diseased) soil samples. Thus, the metrics may be used as an indicator of disease development or spread in a geographical location.

Figure 5:
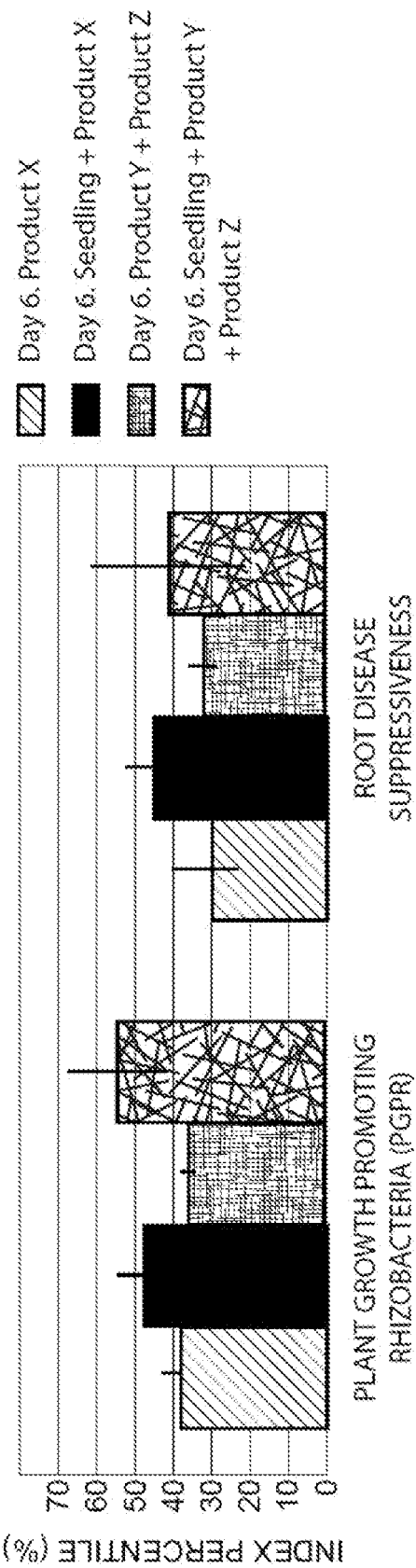
FIG. 5 is a diagram including example metrics of soil samples treated with soybean germinating seeds according to an embodiment.

FIG. 5 is a diagram including example metrics of soil samples treated with soybean germinating seeds according to an embodiment. In comparison with control soil samples, soil samples treated with seedling (e.g., soybean germinated seeds) in addition to one or more products have greater soil health indicator values for plant growth promoting rhizobacteria (PGPR) and root disease resistance. The soil samples were obtained six days after the treatment.

Figure 6:
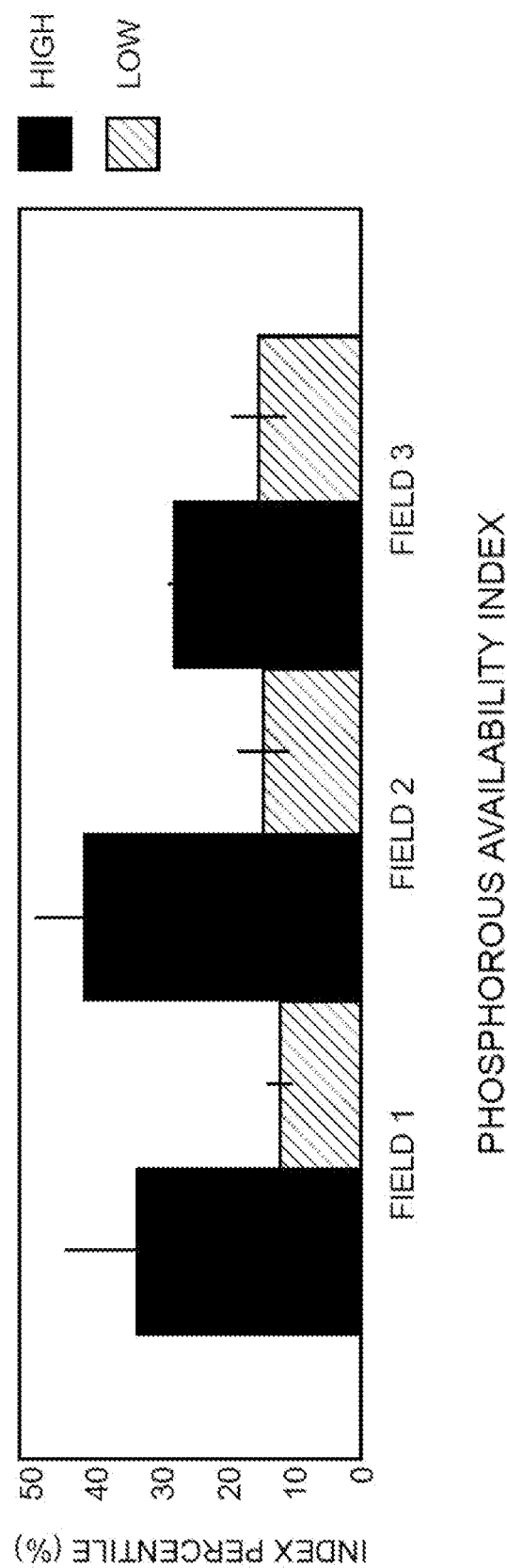
FIG. 6 is a diagram including example metrics of soil samples from different locations within fields according to an embodiment.

FIG. 6 is a diagram including example metrics of soil samples from different locations within fields according to an embodiment. The soil samples were collected from a high productivity area and low productivity area from each of three fields. In comparison with the soil samples from the low productivity areas, soil samples from the high productivity areas have greater soil health indicator values for phosphorous capacity. Thus, growth of crops in the low productivity areas may be negatively impacted by lower availability of nutrients from phosphorous.

FIG. 7 illustrates an example user interface with metrics of soil samples according to an embodiment. In particular, the user interface displays ratios of aerobic microbes to anaerobic microbes (as an indicator of oxygen levels) in soil samples from different farms. In the example shown in FIG. 7, a user may filter metrics of soil samples based on criteria such as sampling start and end dates, farm, field, and treatments. The analytics system 100 may also provide options in the user interface to display information for different types of crops or indicators of nutrients such as carbon, potassium, nitrogen, and phosphorus.

V. Example Microbial Compositions

FIG. 8 is a diagram of an example microbial composition of healthy soil according to an embodiment. FIG. 9 is a diagram of an example microbial composition of compost according to an embodiment. In these examples, the microbial composition of the compost has a greater percentage of Rhizobiales in comparison to the microbial composition of the healthy soil. Rhizobiales are an order of bacteria that fix nitrogen. Accordingly, the analytics system 100 may determine that a soil health indicator associates the microbial composition of the compost with a high nitrogen capacity, e.g., relative to capacity of microbial compositions of typical healthy soil. Additionally, the analytics system 100 may determine that the compost is suitable as a treatment to soils with low nitrogen fixers.

VI. Additional Considerations

The foregoing description of the embodiments of the invention has been presented for the purpose of illustration; it is not intended to be exhaustive or to limit the invention to the precise forms disclosed. Persons skilled in the relevant art can appreciate that many modifications and variations are possible in light of the above disclosure.

Some portions of this description describe the embodiments of the invention in terms of algorithms and symbolic representations of operations on information. These algorithmic descriptions and representations are commonly used by those skilled in the data processing arts to convey the substance of their work effectively to others skilled in the art. These operations, while described functionally, computationally, or logically, are understood to be implemented by computer programs or equivalent electrical circuits, microcode, or the like. Furthermore, it has also proven convenient at times, to refer to these arrangements of operations as modules, without loss of generality. The described operations and their associated modules may be embodied in software, firmware, hardware, or any combinations thereof.

Any of the steps, operations, or processes described herein may be performed or implemented with one or more hardware or software modules, alone or in combination with other devices. In one embodiment, a software module is implemented with a computer program product including a computer-readable non-transitory medium containing computer program code, which can be executed by a computer processor for performing any or all of the steps, operations, or processes described.

Embodiments of the invention may also relate to a product that is produced by a computing process described herein. Such a product may include information resulting from a computing process, where the information is stored on a non-transitory, tangible computer readable storage medium and may include any embodiment of a computer program product or other data combination described herein.

As used herein any reference to "one embodiment" or "an embodiment" means that a particular element, feature, structure, or characteristic described in connection with the embodiment is included in at least one embodiment. The appearances of the phrase "in one embodiment" in various places in the specification are not necessarily all referring to the same embodiment.

As used herein, the terms "comprises," "comprising," "includes," "including," "has," "having" or any other variation thereof, are intended to cover a non-exclusive inclusion. For example, a process, method, article, or apparatus that comprises a list of elements is not necessarily limited to only those elements but may include other elements not expressly listed or inherent to such process, method, article, or apparatus. Further, unless expressly stated to the contrary, "or" refers to an inclusive or and not to an exclusive or. For example, a condition A or B is satisfied by any one of the following: A is true (or present) and B is false (or not present), A is false (or not present) and B is true (or present), and both A and B are true (or present).

Finally, the language used in the specification has been principally selected for readability and instructional purposes, and it may not have been selected to delineate or circumscribe the inventive subject matter. It is therefore intended that the scope of the invention be limited not by this detailed description, but rather by any claims that issue on an application based hereon. Accordingly, the disclosure of the embodiments of the invention is intended to be illustrative, but not limiting, of the scope of the invention, which is set forth in the following claims.

What is claimed is:

1. A method comprising:
   obtaining a soil sample from a geographical location;
   determining a management practice applied to soil at the geographical location;
   determining a plurality of organisms in the soil sample;
   determining, for each of the plurality of organisms, a measure of the organism in the soil sample;
   determining microbial composition of the soil sample using the measures of the organisms;
   determining that the management practice was applied to soil at a plurality of geographical locations within a threshold distance of the geographical location;
   determining reference metrics of a plurality of soil samples from the plurality of geographical locations within the threshold distance of the geographical location, wherein the plurality of soil samples from the plurality of geographical locations provide context to the microbial composition of the soil sample;
   determining a metric of the soil sample by comparing the microbial composition to the reference metrics of the plurality of soil samples from the plurality of geographical locations; and
   transmitting the metric to a client device for display in context of the reference metrics on a user interface.

2. The method of claim 1, wherein determining the metric of the soil sample comprises:
   determining a value of a soil health indicator of the soil sample using the microbial composition;
   determining a distribution of values of the soil health indicator for the soil samples using the reference metrics; and
   determining a percentile of the value with respect to the distribution of values.

3. The method of claim 1, wherein determining the metric of the soil sample further comprises:
   determining one or more of oxygen status, nitrogen capacity, phosphorous capacity, potassium capacity, available carbon, or plant growth promoting bacteria of the soil sample.

4. The method of claim 1, wherein determining the metric of the soil sample further comprises:
   determining a level of root disease suppression or post-harvest degradation of crops grown in the geographical location using the microbial composition.

5. The method of claim 1, further comprising:
   extracting microbial genetic material from the soil sample; and
   generating nucleic acid sequence reads using the microbial genetic material, wherein the measures of the organisms in the soil sample are determined using the nucleic acid sequence reads.

6. The method of claim 1, wherein the management practice includes one or more of: no-till farming, use of a cover crop, carbon farming, strip-till, conservation agriculture, and application of a product.

7. The method of claim 1, further comprising:
   providing a command to a device to apply a treatment the soil at the geographical location based on the metric.

8. The method of claim 1, further comprising:
   receiving metadata indicating the geographical location and the management practice applied to soil at the geographical location.

9. The method of claim 8, wherein the metadata further indicates one or more types of crops grown at the geographical location.

10. A system comprising:
    a sampling tube for obtaining a soil sample from a geographical location;
    a sequencer to determine nucleic acid sequence reads of the soil sample; and
    one or more processors and a memory, the memory storing computer program instructions that when executed by the one or more processors cause the one or more processors to:
    determine a management practice applied to soil at the geographical location;
    receive the nucleic acid sequence reads of the soil sample;
    determine, for each nucleic acid sequence read of at least a subset of the nucleic acid sequence reads, taxonomic information of the nucleic acid sequence read;
    determine microbial composition of the soil sample using the taxonomic information;
    determine that the management practice was applied to soil at a plurality of geographical locations within a threshold distance of the geographical location;
    determine reference metrics of a plurality of soil samples from the plurality of geographical locations within the threshold distance of the geographical location, wherein the plurality of soil samples from the plurality of geographical locations provide context to the microbial composition of the soil sample;
    determine a metric of the soil sample by comparing the microbial composition to the reference metrics of the plurality of soil samples from the plurality of geographical locations; and
    transmit the metric to a client device for display in context of the reference metrics on a user interface.

11. The system of claim 10, wherein determine the metric of the soil sample comprises:
    determine a value of a soil health indicator of the soil sample using the microbial composition;
    determine a distribution of values of the soil health indicator for the soil samples using the reference metrics; and
    determine a percentile of the value with respect to the distribution of values.

12. The system of claim 10, wherein determine the metric of the soil sample further comprises:
    determine one or more of oxygen status, nitrogen capacity, phosphorous capacity, potassium capacity, available carbon, or plant growth promoting bacteria of the soil sample.

13. The system of claim 10, wherein determine the metric of the soil sample further comprises:
    determine a level of root disease suppression of crops grown in the geographical location using the microbial composition.

14. The system of claim 10, wherein determine the metric of the soil sample further comprises:
    determine a level of post-harvest degradation of crops grown in the geographical location using the microbial composition.

15. The system of claim 10, wherein determine the microbial composition of the soil sample using the taxonomic information comprises:
    determine a plurality of organisms in the soil sample;
    determine, for each of the plurality of organisms, a measure of the organism in the soil sample; and
    normalize the measure using a total measure of organisms in the soil sample.

16. The system of claim 10, wherein the management practice includes one or more of: no-till farming, use of a cover crop, carbon farming, strip-till, conservation agriculture, and application of a product.

17. A non-transitory computer-readable storage medium comprising one or more processors and a memory, the memory storing computer program instructions that when executed by the one or more processors cause the one or more processors to:
- determine a plurality of organisms in a soil sample from a geographical location;
- determine a management practice applied to soil at the geographical location;
- determine, for each of the plurality of organisms, a measure of the organism in the soil sample;
- determine microbial composition of the soil sample using the measures of the organisms;
- determine that the management practice was applied to soil at a plurality of geographical locations within a threshold distance of the geographical location;
- determine reference metrics of a plurality of soil samples from the plurality of geographical locations within the threshold distance of the geographical location, wherein the plurality of soil samples from the plurality of geographical locations provide context to the microbial composition of the soil sample;
- determine a metric of the soil sample by comparing the microbial composition to the reference metrics of the plurality of soil samples from the plurality of geographical locations; and
- transmit the metric to a client device for display in context of the reference metrics on a user interface.

18. The non-transitory computer-readable storage medium of claim 17, storing further computer program instructions that when executed by the one or more processors cause the one or more processors to:
- determine a value of a soil health indicator of the soil sample using the microbial composition;
- determine a distribution of values of the soil health indicator for the soil samples using the reference metrics; and
- determine a percentile of the value with respect to the distribution of values.

19. The non-transitory computer-readable storage medium of claim 17, storing further computer program instructions that when executed by the one or more processors cause the one or more processors to:
- determine one or more of oxygen status, nitrogen capacity, phosphorous capacity, potassium capacity, available carbon, or plant growth promoting bacteria of the soil sample.

20. The non-transitory computer-readable storage medium of claim 17, wherein the management practice includes one or more of: no-till farming, use of a cover crop, carbon farming, strip-till, conservation agriculture, and application of a product.

* * * * *

UNITED STATES PATENT AND TRADEMARK OFFICE
CERTIFICATE OF CORRECTION

PATENT NO. : 11,821,887 B2
APPLICATION NO. : 16/258415
DATED : November 21, 2023
INVENTOR(S) : Parameswaran et al.

It is certified that error appears in the above-identified patent and that said Letters Patent is hereby corrected as shown below:

In the Claims

In Column 17, in Claim 7, Line 59, delete "treatment the" and insert -- treatment of the --, therefor.

Signed and Sealed this
Twenty-first Day of May, 2024

Katherine Kelly Vidal
*Director of the United States Patent and Trademark Office*